United States Patent
Popp et al.

(10) Patent No.: US 6,699,464 B1
(45) Date of Patent: Mar. 2, 2004

(54) COMPOSITIONS FOR TREATMENT OF HYPERPIGMENTATION AND METHODS FOR MAKING AND USING SUCH COMPOSITIONS

(75) Inventors: Karl F. Popp, Schodack Landing, NY (US); Kathleen L. Clark, Medusa, NY (US)

(73) Assignee: Stiefel Laboratories, Inc., Coral Gables, FL (US)

( * ) Notice: Subject to any disclaimer, the term of this patent is extended or adjusted under 35 U.S.C. 154(b) by 0 days.

(21) Appl. No.: 10/208,279

(22) Filed: Jul. 30, 2002

Related U.S. Application Data

(60) Provisional application No. 60/308,781, filed on Jul. 30, 2001.

(51) Int. Cl.$^7$ ................................................ A61K 7/48
(52) U.S. Cl. ........................ 424/62; 424/401; 424/725
(58) Field of Search ........................ 424/401, 62, 725

(56) References Cited

U.S. PATENT DOCUMENTS

| | | | |
|---|---|---|---|
| 4,136,166 A | 1/1979 | Barnett et al. | 424/62 |
| 5,378,461 A | 1/1995 | Neigut | 424/94.1 |
| 5,886,041 A | 3/1999 | Yu et al. | 514/557 |
| 5,932,612 A | 8/1999 | Gordon et al. | 514/458 |
| 6,048,517 A | 4/2000 | Kaplan | 424/60 |
| 6,048,886 A | 4/2000 | Neigut | 514/412 |

FOREIGN PATENT DOCUMENTS

| | | |
|---|---|---|
| WO | WO 95/26180 | 10/1995 |
| WO | WO 97/12591 | 4/1997 |

OTHER PUBLICATIONS

Sauermann et al., "Coenzyme Q10—A Cutaneous Antioxidant and Energizer," Kosmetische Medizin, 20 Ausgabe 1, pp. 22–25, Apr. 1999.
Ajinomoto Co., Inc., "The Salts of PCA and their Moisturizing Effects," Technical Bulletin, 13 pages, Feb. 15, 1978.
Physicians' Desk Reference, 29$^{th}$ Ed., Medical Economics Company, p. 773, 1975.
Physicians' Desk Reference, 32$^{nd}$ Ed., Litton Industries, Inc., pp. 846–847, 1978.
Clinical Pharmacology 2000—Monograph for Hydroquinone, 1 page, Jan. 22, 2001, at http://cp.gsm.com/apps/product/showmono.asp?cpnum=1377&monotype=full&match=0.
Fytokem Products Inc., Fytokem Product Technical Information for Tyrostat–20, 2 pages, Apr. 5, 1999.
Fytokem Products Inc., Fytokem Product Technical Information for Tyrostat–21, 2 pages, Jan. 17, 2000.
Ajinomoto Co., Inc., "Ajinomoto Co.'s Humectant AJIDEW, Applications for Cosmetics," Technical Bulletin, 9 pages, Jun. 1972.
ICN Pharmaceuticals, Inc., "Glyquin" Product Sheet, 2 pages, May, 2000.
Ajinomoto Co., Inc., "Ajinomoto Co.'s AJIDEW," Technical Bulletin, 19 pages, Dec. 1972.

*Primary Examiner*—Jyothsna Venkat
(74) *Attorney, Agent, or Firm*—Jenkens & Gilchrist

(57) ABSTRACT

A composition for treatment of hyperpigmentation having a SPF value of at least 15 includes hydroquinone, sunscreens, antioxidants and emulsifiers and emollients. The composition can be made into an emulsion having physical and chemical stability for a prolonged period of time over a wide range of temperatures.

4 Claims, No Drawings

COMPOSITIONS FOR TREATMENT OF HYPERPIGMENTATION AND METHODS FOR MAKING AND USING SUCH COMPOSITIONS

CROSS-REFERENCES TO RELATED APPLICATIONS

This application claims priority to U.S. Provisional Application Serial No. 60/308,781, entitled "Compositions for Treatment of Hyperpigmentation and Methods for Making and Using Such Compositions," filed on Jul. 30, 2001.

FIELD OF THE INVENTION

This invention relates to treating hyperpigmentation. In particular, it relates to compositions for treating hyperpigmentation of human skin which can offer protection from UVA and/or UVB radiation and further relates to methods for making and using such compositions.

BACKGROUND OF THE INVENTION

Aging, birth control pills, pregnancy, and certain types of skin injuries can cause dark areas on the skin. This condition is usually referred to as hyperpigmentation. Certain compounds have been found to reduce or eliminate hyperpigmentation when they are introduced into the affected skin areas. One approach to treating hyperpigmentation is by placing a compound which reduces hyperpigmentation on the skin.

Generally, the compound which reduces hyperpigmentation is incorporated into a cream which is placed on the skin. It is desirable to have a hyperpigmentation-treating compound that is incorporated in a cream which soaks into the skin without leaving a residue. Such creams are often referred to as vanishing creams. The only FDA-approved product for treatment of hyperpigmentation is hydroquinone. Hydroquinone has been found effective in reducing hyperpigmentation when applied to the affected skin areas. Hydroquinone, however, causes skin irritation. Accordingly, hydroquinone must be applied with ingredients which reduce or eliminate skin irritation of hydroquinone. Topical formulations of hydroquinone for treating hyperpigmentation have been marketed in the United States under the names Eldoquin®, Eldopaque-Forte®, Eldoquin® Forte, and Glyquin®. Hydroquinone products lighten the color of the skin areas to which it is applied by killing off the melanin making cells—the melanocytes.

Typical amounts of hydroquinone in a skin lightening product range from two to four percent. Over-the-counter brands contain about two percent, while prescription strength formulations contain up to four percent. The maximum level marketed as a prescription product is four percent.

Additionally, the composition containing hydroquinone must satisfy a number of requirements to be commercially acceptable. First, the composition must have certain cosmetic properties. A cream must be chemically and physically stable, at both normal and high temperatures for a prolonged period of time. Second, the composition must also be readily absorbable by the skin, and have a smooth texture and appealing color. Finding the right combination of ingredients that provides these characteristics is a difficult process, and involves art as well as science. Unless these factors are satisfied, the product will not be appealing to consumers and will not provide effective relief.

Hyperpigmentation is aggravated by exposure to ultraviolet rays. Accordingly, a product that treats hyperpigmented skin conditions and reduces exposure to ultraviolet radiation is particularly desirable. It is well known that exposure to ultraviolet radiation after the use of a skin lightening preparation can result in harmful side effects, and render the product useless. The use of sunscreens in a skin lightening preparation reduces the effects of exposure to the harmful rays of the sun, and allows a user to be exposed to the sun after application.

Certain compounds are known to provide protection from UVA and UVB radiation. The level of protection is measured as the sun protection factor, or SPF. The SPF of a formulation is defined as the multiple of time that this formulation will prevent reddening of the skin when compared to the exposure time that causes unprotected skin to exhibit reddening. For instance, a person wearing a sunscreen that has a SPF value of 15 can remain in the sun for 15 times longer than a person with no sunscreen protection. It is generally recognized that to be clinically effective, a sunscreen should have a SPF value of at least 15.

The SPF level of a formulation containing many ingredients (such as a vanishing cream) cannot be easily predicted because of the interaction between ingredients. Other ingredients, particularly hydroquinone, can affect the SPF values of a formulation in an unpredictable manner. Thus, the art of developing hyperpigmentation formulations that have the necessary characteristics of a cream and that also provide WVA and UVB protection of at least SPF 15 is highly unpredictable.

The present invention overcomes the inherent problems and provides desirable compositions and methods for making and using them.

SUMMARY OF THE INVENTION

In accordance with one aspect of the present invention, a well tolerated composition for treating hyperpigmentation includes hydroquinone and provides UVA and UVB protection with a SPF value of at least 15. In accordance with another aspect of the present invention, a well tolerated hydroquinone-based composition has UVA and UVB protection of at least 15 and is in a form of a cream which is readily absorbable by the skin, chemically and physically stable, and has a smooth texture and a homogeneous appearance.

In accordance with a further aspect of the present invention, a composition that reduces darkening of the skin due to hyperpigmentation contains hydroquinone, antioxidants, sunscreens, moisturizers, and rumex extracts and is well tolerated when applied to humans, is chemically and physically stable for a prolonged period of time over a range of temperatures encountered in storage and transportation, has a SPF value of at least 15 and has a cosmetically elegant appearance.

DETAILED DESCRIPTION OF THE INVENTION

It has been discovered that a well tolerated composition for treating hyperpigmentation using hydroquinone can be formulated to provide UVA and UVB protection with a SPF value of at least 15. It has been further discovered that such composition can be formulated into a cream which has a smooth texture, a homogeneous, pleasing appearance and is readily absorbable by the skin. It has been also discovered that such composition can be formulated to be physically and chemically stable for a prolonged period of time even when exposed to a wide range of temperatures which may be encountered in transporting and storing the cream.

The ingredient of the present formulation that is responsible for treating hyperpigmentation is hydroquinone. The concentration of hydroquinone in the formulation is sufficiently high to be effective in treating hyperpigmentation but sufficiently low to avoid a loss of acceptable stability of the formulation. Generally, the concentration of hydroquinone is in the range from about 1% to about 10% by weight of the formulation that is applied to the skin. Preferably, the concentration of hydroquinone is in the range from about 2 percent to about 4 percent by weight of the formulation. Particularly preferred are formulations containing hydroquinone at about 4 percent by weight of the formulation.

Formulations containing hydroquinone have been known to produce irritation, redness, sensitization, and burning. Therefore, to produce a well tolerated composition based on hydroquinone, it is necessary to include other ingredients that reduce the adverse effects of hydroquinone on human skin. The composition of the present invention is well tolerated by humans and does not produce redness, sensitization or burning when applied to human skin. It is presently believed that the reduction of the adverse effects of hydroquinone on human skin is primarily attributed to sodium pyrrolidone carboxylate (sodium PCA). Generally, the concentration of sodium PCA is in the range from about 1 percent to about 10 percent by weight of the formulation.

The compositions of the present invention include sunscreens which in combination with other ingredients provide a composition which has a SPF of at least 15. To provide a formula with a SPF value of not less than 15 usually requires the use of more than a single UVB sunscreen. Suitable UVB sunscreens for use in the compositions of the present invention include avobenzone, octyl methoxycinnamate, oxybenzone and octocrylene. Avobenzone additionally functions as the preferred UVA sunscreen, however it is not measured as part of the SPF value. The amount of octyl methoxycinnamate ranges from 1 percent to 10 percent, the amount of octocrylene ranges from 1 percent to 15 percent, and the amount of oxybenzone ranges from 0 percent to 10 percent by weight of the formulation. The amount of avobenzone in the formulation ranges from 1 percent to 5 percent. "Octyl methoxycinnamate" has been renamed "octinoxate." However, the compound is the same under either name.

The concentration of sunscreens in the composition of the present invention is generally in the range from about 13 percent to about 27 percent by weight of the formulation, and preferably from about 15 percent to about 22 percent by weight of the formulation. Particularly preferred percentage of sunscreen is about 16.5 percent by weight of the formulation.

The composition of the present invention can also include antioxidants which enhance the dermatologically useful effect of the formulation. Generally, the concentration of antioxidants is in the range from about 0.02 percent to about 1 percent by weight of the formulation, and preferably in the range from about 0.05 percent to about 0.5 percent by weight of the formulation. Any antioxidants which are compatible with the present formulation can be used. Examples of suitable antioxidants include sodium metabisulfite and propyl gallate.

Emulsifiers and emollients are used to provide a suitable texture and impart the characteristics of a vanishing cream. Any suitable emollients and emulsifiers can be used in the present composition. Examples of suitable emulsifiers/emollients include: ceteareth-20, cetostearyl alcohol, diethylaminethyl stearate, glyceryl dilaurate, glyceryl monostearate, glyceryl stearate, PEG-100 stearate, octyldodecyl stearoyl stearate, polysorbate 80, quaternium-26, stearyl alcohol. The emulsifiers and emollients generally comprise from 20 percent to 50 percent by weight of the formulation, and preferably from 30 percent to 40 percent by weight of the formulation.

Other moisturizers include sodium PCA, dimethicone, cyclomethicone, propylene glycol and polysiloxane derivatives.

The composition of the present invention can also include rumex extract to enhance the hydroquinone activity. Extracts of rumex occidentalis are commercially available, for example, as Tyrostat-20 or Tyrostat-21.

The stability of the present composition is enhanced and the acceptable pH is achieved by pH modifiers, such as, citric acid, phosphoric acid or lactic acid.

Hydroxyethyl cellulose may be added as a viscosity stabilizer.

A chelating agent, such as disodium edetate, can also be used to stabilize the composition of the present invention.

The present formulation can also include antimicrobial preservatives, such as methylparaben and propylparaben.

Preferred Embodiments

Preferred embodiments of this invention contain hydroquinone at 2 percent to 4 percent by weight of the formulation for an effective dose that reduces dark areas due to hyperpigmentation.

The antioxidants most suitable for this formulation include propyl gallate and sodium metabisulfite in an amount necessary to provide effective delivery of the hydroquinone, ranging from 0.02 percent to 0.2 percent by weight of the formulation.

This invention also contains moisturizers, such as sodium PCA and ubiquinone, in an amount that reduces irritation, typically in the range of 1 percent to 10 percent by weight of the formulation for sodium PCA, and 0.2 percent to 5 percent by weight of the formulation for ubiquinone in a fatty acid carrier, such as squalane.

Sunscreens that provide maximum protection for UVB radiation without compromising stability include octyl methoxycinnamate, oxybenzone, and octocrylene, or combinations thereof Octyl methoxycinnamate has a preferred range of 4.0 percent to 7.5 percent, octocrylene has a preferred range of 6 percent to 10 percent, and oxybenzone has a preferred range of three percent to six percent by weight of the formulation. A sunscreen such as avobenzone can be used at lower amounts for protection from UVA radiation, such as 1 percent to 5 percent by weight of the formulation, with a preferred range of 2 percent to 3 percent by weight of the formulation.

A preferred method of making the composition includes boiling and then cooling 30.25 to 36.25 parts of water to 75 degrees C., and dissolving 0.10 part of edetate disodium, 0.05 part of methyl paraben, and 0.03 part of sodium metabisulfite to form a first solution; this is followed by cooling the first solution, and dissolving 1.2 parts of citric acid and then adding 3.4 parts of propylene glycol, 2.5 parts of sodium PCA as a 50% aqueous solution, 0.3 part of hydroxyethyl cellulose, and 4.0 parts of hydroquinone to form a second solution.

Next, the following ingredients, expressed in "parts" as percent by weight of ingredient by percent by weight formulation, are combined and heated to 65 degree C. to form a uniform composition: 0 or 6.0 parts of oxybenzone, 9.0 parts of glyceryl monostearate, 6.5 parts of octyldodecyl stearoyl stearate, 2.45 parts of quaternium-26, 5.0 parts of glyceryl stearate and PEG-100 stearate, 3.9 parts of glyceryl dilaurate, 0.9 part of diethylaminoethyl stearate, 2.3 parts of cetostearyl alcohol, 2.2 parts of ceteareth-20, 0.5 part of dimethicone, 0.35 part of polysobrate 80, 1.4 parts of stearyl alcohol, 3.0 parts of avobenzone, 0.05 part of propylparaben, 0.1 part of propyl gallate, 1.0 part of a squalane and ubiquinone solution, and 7.5 parts octyl methoxycinnamate; this is added to the second solution to achieve a uniform combined composition.

After cooling the uniform combined composition, 0.02 part of sodium metabisulfite is dissolved in 5 parts of boiling water to produce a solution that is added to the combined composition; the remaining 1.0 part of rumex extract is next added to the combined composition with cooling to produce a homogeneous, uniform composition.

EXAMPLES

The following examples are provided to further illustrate the present invention. They are not intended to limit the scope of the present invention but merely to disclose the compositions which are currently most preferred.

Example 1

The following composition was prepared in accordance with the present invention:

| Composition for Treating Hyperpigmentation with UVA and UVB Sunscreens | |
|---|---|
| Ingredients | Percentage (% W/W) |
| Hydroquinone | 4.00 |
| Avobenzone | 3.00 |
| Ceteareth-20 | 2.20 |
| Cetostearyl Alcohol | 2.30 |
| Citric Acid | 1.20 |
| Diethylaminoethyl Stearate | 0.90 |
| Dimethicone | 0.50 |
| Edetate Disodium | 0.10 |
| Glyceryl Dilaurate | 3.90 |
| Glyceryl Monostearate | 9.00 |
| Glyceryl Stearate (and) PEG-100 Stearate | 5.00 |
| Hydroxyethyl Cellulose | 0.30 |
| Methylparaben | 0.05 |
| Octyldodecyl Stearoyl Stearate | 6.50 |
| Octyl Methoxycinnamate | 7.50 |
| Polysorbate 80 | 0.35 |
| Propylene Glycol | 3.40 |
| Propyl Gallate | 0.10 |
| Propylparaben | 0.05 |
| Purified Water | 41.25 |
| Quaternium-26 | 2.45 |
| Rumex Extract (as Tyrostat-20) | 1.00 |
| Sodium Metabisulfite | 0.05 |
| Sodium PCA, 50% solution | 2.50 |
| Squalane (and) Ubiquinone | 1.00 |
| Stearyl Alcohol | 1.40 |

The above defined composition had smooth texture and was homogeneous. The composition was determined to be a vanishing cream in that it readily soaked into the human skin.

Example 2

The composition of Example 1 was subjected to a range of temperatures over a period of time from 30 to 90 days to determine the chemical stability of selected ingredients.

First, the stability of hydroquinone was analyzed for a period of 30 and 90 days at temperatures of 6° C., 25° C., 30° C. and 40° C. using a suitable, high pressure liquid chromatographic(HPLC) assay. "FT" refers to freeze thaw conditions (−10° to −20° C.) where the product is exposed to freezing conditions for two days and then allowed to that at controlled room temperature (15° to 30° C.) for the next five days. The %W/W results obtained are shown in Table 1 below:

TABLE 1

| DAYS | FT | 6° | 25° | 30° | 40° |
|---|---|---|---|---|---|
| 30 |  | 3.94 | 3.97 | 3.95 | 3.98 |
| 90 | 3.95 | 3.95 | 3.94 | 3.96 | 3.97 |

These results show that hydroquinone remains active when exposed to low and high temperatures for 30 and 90 days.

Next, chemical stability of avobenzone was determined using a suitable HPLC assay. The %W/W results obtained are shown in Table 2 below:

TABLE 2

| DAYS | FT | 6° | 25° | 30° | 40° |
|---|---|---|---|---|---|
| 30 |  | 3.26 |  |  |  |
| 30 |  |  | 3.29 |  |  |
| 30 |  |  |  | 3.28 |  |
| 30 |  |  |  |  | 3.30 |
| 90 | 3.25 |  |  |  |  |
| 90 |  |  | 3.25 |  |  |
| 90 |  |  |  | 3.23 |  |
| 90 |  |  |  | 3.26 |  |
| 90 |  |  |  |  | 3.26 |

The results show that avobenzene remained active after exposure of the formulation to high and low temperatures for 30 and 90 days.

Next, chemical stability of Octyl Methoxycinnamate was determined using a suitable HLPC assay. The %W/W results obtained are shown in Table 3 below:

TABLE 3

| DAYS | FT | 6° | 25° | 30° | 40° |
|---|---|---|---|---|---|
| 30 |  | 7.59 |  |  |  |
| 30 |  |  | 7.62 |  |  |
| 30 |  |  |  | 7.62 |  |
| 30 |  |  |  |  | 7.75 |
| 90 | 7.99 |  |  |  |  |
| 90 |  |  | 8.06 |  |  |
| 90 |  |  |  | 7.97 |  |
| 90 |  |  |  | 7.91 |  |
| 90 |  |  |  |  | 8.05 |

The results show that octyl methoxycinnamate remained chemically active after exposure of the formulation to high and low temperatures for 30 and 90 days.

Next, the formulations subjected to 6, 25, 30 and 40 degree temperatures for 30 to 90 days were visually examined for appearance and changes in appearance. The results obtained are shown in Table 4 below.

TABLE 4

| DAY | APPEARANCE: |
|---|---|
| 0 | A very pale yellow, homogeneous, smooth cream. |
| 30 | Appearance of all samples: unchanged. |

TABLE 4-continued

| DAY | APPEARANCE: |
|---|---|
| 60 | Appearance of all samples: unchanged. |
| 90 | 40° C. beginning to discolor very slightly. Appearance of all samples unchanged. |

Next, the package was examined and the results are summarized in Table 5.

TABLE 5

| DAY | APPEARANCE: Package |
|---|---|
| 0 | 9.5 dram glass vial, with polyseal cap. |
| 30 | Same as initial. |
| 60 | Same as initial. |
| 90 | Same as initial. |

This formulation exhibits acceptable chemical stability for 90 days from 6° C. to 40° C. and physical stability for 90 days from freeze thaw to 40° C.

Example 3

The following composition was prepared in accordance with the present invention:

| Composition for Treating Hyperpigmentation with UVA and UVB Sunscreens | |
|---|---|
| Ingredients | Percentage (% W/W) |
| Hydroquinone | 4.00 |
| Avobenzone | 3.00 |
| Ceteareth-20 | 2.20 |
| Cetostearyl Alcohol | 2.30 |
| Citric Acid | 1.20 |
| Diethylaminoethyl Stearate | 0.90 |
| Dimethicone | 0.50 |
| Edetate Disodium | 0.10 |
| Glyceryl Dilaurate | 3.90 |
| Glyceryl Monostearate | 9.00 |
| Glyceryl Stearate (and) PEG-100 Stearate | 5.00 |
| Hydroxyethyl Cellulose | 0.30 |
| Methylparaben | 0.05 |
| Octyldodecyl Stearoyl Stearate | 6.50 |
| Octyl Methoxycinnamate | 7.50 |
| Oxybenzone | 6.00 |
| Polysorbate 80 | 0.35 |
| Propylene Glycol | 3.40 |
| Propyl Gallate | 0.10 |
| Propylparaben | 0.05 |
| Purified Water | 35.25 |
| Quaternium-26 | 2.45 |
| Rumex Extract (as Tyrostat-20) | 1.00 |
| Sodium Metabisulfite | 0.05 |
| Sodium PCA, 50% solution | 2.50 |
| Squalane (and) Ubiquinone | 1.00 |
| Stearyl Alcohol | 1.40 |

Example 4

The composition of Example 3 was subjected to a range of temperatures over a prolonged period of time to determine the chemical stability of selected ingredients.

First, the stability of hydroquinone was analyzed for a period of 30 to 90 days at temperature of 6° C., 25° C., 30° C., and 40° C. using a suitable HPLC assay. The % W/W results obtained are shown in Table 6 below.

TABLE 6

| DAYS | FT | 6° | 25° | 30° | 40° |
|---|---|---|---|---|---|
| 0 | | | 3.95 | | |
| 30 | | | 3.99 | | |
| 30 | | | | 3.99 | |
| 30 | | | | | 4.01 |
| 60 | | | 4.04 | | |
| 60 | | | | 3.99 | |
| 60 | | | | | 3.90 |
| 90 | 4.02 | | | | |
| 90 | | 3.98 | | | |
| 90 | | | | 3.99 | |
| 90 | | | | 3.99 | |
| 90 | | | | | 3.98 |

The results show that hydroquinone remained active after exposure of the formulation to high and low temperatures for 30 to 90 days.

Next, chemical stability of avobenzone was determined using a suitable HPLC assay. The %W/W results obtained are shown in Table 7 below:

TABLE 7

| DAYS | FT | 6° | 25° | 30° | 40° |
|---|---|---|---|---|---|
| 0 | | | 3.03 | | |
| 30 | | | 2.99 | | |
| 30 | | | | 2.98 | |
| 30 | | | | | 3.01 |
| 60 | | | 2.94 | | |
| 60 | | | | 2.94 | |
| 60 | | | | | 2.93 |
| 90 | 2.93 | | | | |
| 90 | | 2.87 | | | |
| 90 | | | | 2.92 | |
| 90 | | | | 2.93 | |
| 90 | | | | | 2.93 |

The results show that avobenzene remained active after exposure of the formulation to high and low temperatures for 30 to 90 days.

Next, the chemical stability of octyl methoxycinnamate was determined using a suitable HPLC assay. The %W/W results obtained are shown in Table 8 below:

TABLE 8

| DAYS | FT | 6° | 25° | 30° | 40° |
|---|---|---|---|---|---|
| 0 | | | 7.61 | | |
| 30 | | | 7.71 | | |
| 30 | | | | 7.69 | |
| 30 | | | | | 7.74 |
| 60 | | | 7.43 | | |
| 60 | | | | 7.46 | |
| 60 | | | | | 7.46 |
| 90 | 7.57 | | | | |
| 90 | | 7.97 | | | |
| 90 | | | | 7.96 | |
| 90 | | | | 8.00 | |
| 90 | | | | | 8.03 |

The results show that octyl methoxycinnamate remained active after exposure of the formulation to high and low temperatures for 30 to 90 days.

Next, the chemical stability of the oxybenzone sunscreen was determined for 30° C., 25° C., 30° C., and 40° C. using a suitable HPLC assay. The %W/W results obtained are shown in Table 9 below:

TABLE 9

| DAYS | FT | 6° | 25° | 30° | 40° |
|---|---|---|---|---|---|
| 0 | | | 6.07 | | |
| 30 | | | 5.98 | | |
| 30 | | | | 5.95 | |
| 30 | | | | | 6.04 |
| 60 | | | 6.04 | | |
| 60 | | | | 6.02 | |
| 60 | | | | | 6.07 |

The results show that the oxybenzone sunscreen remained active after exposure of the formulation to high and low temperatures for 30 to 60 days.

Next, the chemical stability of the oxybenzone sunscreen at 90 days was determined using a suitable HPLC assay. The %W/W results obtained are shown in Table 10 below:

TABLE 10

| DAYS | FT | 6° | 25° | 30° | 40° |
|---|---|---|---|---|---|
| 90 | 6.09 | | | | |
| 90 | | 6.05 | | | |
| 90 | | | 6.09 | | |
| 90 | | | | 6.07 | |
| 90 | | | | | 6.06 |

The results show that the oxybenzone sunscreen remained active after exposure of the formulation to high and low temperatures for 30 to 90 days.

Next, the composition and coated aluminum tube container were visually examined at 30, 60, and 90 days for their physical stability. The results are summarized in Tables 11 and 12, respectively:

TABLE 11

| DAY | APPEARANCE: product |
|---|---|
| 0 | A very pale yellow, homogeneous, smooth cream. |
| 30 | 40° C. is beginning to discolor, tan very slightly. All others remain as initial. |
| 60 | From 40° C. to 6° C. as day 30. |
| 90 | 40° C. very slightly discolored. All others as initial. |

This formulation exhibits acceptable chemical and physical stability for 90 from freeze/thaw to 40° C.

TABLE 12

| DAY | APPEARANCE: package |
|---|---|
| 0 | 9.5 dram glass vial, with polyseal cap. |
| 30 | Same as initial. |
| 60 | Same as initial. |
| 90 | Same as initial. |

Various changes and modifications will occur to those skilled in the art upon studying this disclosure. All such changes which fall within the spirit of this invention are intended to be included within the scope of the expanded claims.

We claim:

1. A physically and chemically stable vanishing cream for the treatment of hyperpigmentation and having SPF of at least 15, said cream comprising the following ingredients at concentrations expressed in weight percentages based on the weight of the cream: 2 to 4 percent hydroquinone; 3 percent avobenzone; 2.2 percent ceteareth-20; 2.3 percent cetostearyl alcohol; 1.2 percent citric acid; 0.9 percent diethylaminoethyl stearate; 0.5 percent dimethicone; 0.1 percent edetate disodium; 3.9 percent glyceryl dilaurate; 9 percent glyceryl monostearate; 5 percent glyceryl stearate and PEG-100 stearate; 0.3 percent hydroxyethyl cellulose, 0.05 percent methylparaben, 6.5 percent octyldocecyl stearoyl stearate; 7.5 percent octyl methoxycinnamate; 0.35 percent polysorbate 80; 3.4 percent propylene glycol, 0.1 percent propyl gallate; 0.05 percent propylparaben; 2.45 percent quaternium-26; 1 percent rumex occidentalis extract; 0.05 percent sodium metabisulfite; 1 to 10 percent sodium PCA, 1 percent squalane and ubiquinone; 1.4 percent stearyl alcohol; the remaining being purified water; said cream having a SPF value of at least 15.

2. A method for making a physically and chemically stable vanishing cream for the treatment of hyperpigmentation and for providing SPF of at least 15, said method comprising the following steps:
    (a) heating water until it boils,
    (b) cooling the boiled water to 75 degrees C.;
    (c) dissolving 0.10 part edetate disodium, 0.05 part methyl paraben, and 0.03 part sodium metabisulfite in the water to form a first solution;
    (d) cooling the first solution to 47 degree C.;
    (e) dissolving 0.2 parts citric acid in the first solution with stirring to form a second solution;
    (f) adding 3.4 parts propylene glycol, 1 to 10 parts sodium PCA, 0.3 part hydroxyethyl cellulose, and 2.0 to 4.0 parts hydroquinone to the second solution and mixing said second solution until a uniform composition is achieved;
    (g) combining 9.0 parts glyceryl monostearate, 6.5 parts octyldodecyl stearoyl stearate, 2.45 parts quaternium-26, 5.0 parts glyceryl stearate and PEG-100 stearate, 3.9 parts glyceryl dilaurate, 0.9 part diethylaminoethyl stearate, 2.3 parts cetostearyl alcohol, 2.2 parts ceteareth-20, 0.5 part dimethicone, 0.35 part polysobrate 80, 1.4 parts stearyl alcohol, 3.0 parts avobenzone, 0.5 part propylparaben, 0.1 part propyl gallate, 1.0 part squalane and ubiquinone, and 7.5 parts octyl methoxycinnamate;
    (h) heating the mixture in part (g) to a temperature in the range of 60–65 degree C. to melt the solid ingredients;
    (i) stirring the molten mixture to form a uniform composition;
    (j) adding the composition of step (f) and the composition of step (i) to achieve a uniform combined composition;
    (k) cooling the combined composition to 35 degree C.;
    (l) boiling 5 parts water;
    (m) dissolving 0.02 part sodium metabisulfite in the boiling water to produce a solution;
    (n) mixing the solution with the combined composition to produce a uniform composition;
    (o) mixing 1.0 part rumex occidentalis extract with the uniform composition to produce a homogenous mixture;
    (p) cooling the uniform composition.

3. A physically and chemically stable vanishing cream for the treatment of hyperpigmentation, said cream comprising the following ingredients at concentrations expressed in weight percentages based on the weight of the cream: 2 to 4 percent hydroquinone, 3 percent avobenzone, 2.2 percent ceteareth-20, 2.3 percent cetostearyl alcohol, 1.2 percent citric acid, 0.9 percent diethylaminoethyl stearate, 0.5 percent dimethicone, 0.1 percent edetate disodium, 3.9 percent glyceryl dilaurate, 9 percent glyceryl monostearate, 5 percent glyceryl stearate and PEG-100 stearate, 0.3 percent hydroxyethyl cellulose, 0.05 percent methylparaben, 6.5 percent octyldocecyl stearoyl stearate, 7.5 percent octyl methoxycinnamate, 6 percent oxybenzone, 0.35 percent polysorbate 80, 3.4 percent propylene glycol, 0.1 percent propyl gallate, 0.05 percent methylparaben, 2.45 percent quaternium-26, 1 percent rumex occidentalis extract percent sodium metabisulfite, 1 to 10 percent sodium PCA, 1 percent squalane and ubiquinone, 1.4 percent stearyl alcohol, the remaining being purified water, and said cream having a SPF value of at least 15.

4. A method for making a physically and chemically stable vanishing cream for the treatment of hyperpigmentation and for providing SPF of at least 15, said method comprising the following steps:

(a) heating water until it boils;

(b) dissolving 0.10 part edetate disodium, 0.05 part methyl paraben, and 0.03 part sodium metabisulfite in the water to form a first solution;

(c) cooling the first solution to 47 degree C.;

(d) dissolving 1.2 parts citric acid in the first solution with stirring to form a second solution;

(e) adding 3.4 parts propylene glycol, 1 to 10 parts sodium PCA, 0.3 part hydroxyethyl cellulose, and 2.0 to 4.0 parts hydroquinone to the second solution and mixing said second solution until a uniform composition is achieved;

(f) combining 6.0 parts oxybenzone, 9.0 parts glyceryl monostearate, 6.5 parts octyldodecyl stearoyl stearate, 2.45 parts quaternium-26, 5.0 parts glyceryl stearate and PEG-100 stearate, 3.9 parts glyceryl dilaurate, 0.9 part diethylaminoethyl stearate, 2.3 parts cetostearyl alcohol, 2.2 parts ceteareth-20, 0.5 part dimethicone, 0.35 part polysobrate 80, 1.4 parts stearyl alcohol, 3.0 parts avobenzone, 0.05 part propylparaben, 0.1 part propyl gallate, 1.0 part squalane and ubiquinone, and 7.5 parts octyl methoxycinnamate;

(g) heating the mixture of step (f) to 60–65 degree C. to melt the ingredients;

(h) stirring the molten mixture to form a uniform composition;

(i) adding the composition of step (e) and the composition of step (h) and mixing to achieve a uniform combined composition;

(j) cooling the combined composition to 35 degree C.;

(k) boiling 5 parts water;

(l) dissolving 0.02 part sodium metabisulfite in the boiling water to produce a solution;

(m) mixing the mixture with the combined composition to produce a uniform composition;

(n) mixing 1.0 part rumex occidentalis extract with the uniform composition to produce a homogeneous mixture;

(o) cooling the uniform composition.

* * * * *

UNITED STATES PATENT AND TRADEMARK OFFICE
CERTIFICATE OF CORRECTION

PATENT NO. : 6,699,464 B1
DATED : March 2, 2004
INVENTOR(S) : Popp et al.

It is certified that error appears in the above-identified patent and that said Letters Patent is hereby corrected as shown below:

<u>Column 2,</u>
Line 27, change "WVA" to -- UVA --.

<u>Column 10,</u>
Line 28, change "0.2 parts citric acid" to -- 1.2 parts citric acid --.
Line 42, change "0.5 part propylparaben" to -- 0.05 part propylparaben --.

<u>Column 11,</u>
Line 10, change "0.05 percent methylparaben" to -- 0.05 percent propylparaben --.

Signed and Sealed this

Twenty-seventh Day of July, 2004

JON W. DUDAS
*Acting Director of the United States Patent and Trademark Office*